(12) United States Patent
DeGrado et al.

(10) Patent No.: US 6,362,352 B1
(45) Date of Patent: Mar. 26, 2002

(54) F18-LABELED THIA FATTY ACIDS AND METHODS OF MAKING AND USING THE SAME

(75) Inventors: Timothy R. DeGrado; Shuyan Wang, both of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/543,899

(22) Filed: Apr. 6, 2000

Related U.S. Application Data

(60) Provisional application No. 60/129,913, filed on Apr. 19, 1999.

(51) Int. Cl.$^7$ ................................................ C07B 45/00
(52) U.S. Cl. ........................................ 554/85; 554/225
(58) Field of Search ..................... 554/225, 85; 424/9.4

(56) References Cited

U.S. PATENT DOCUMENTS

| | | | | |
|---|---|---|---|---|
| 4,323,547 A | * | 4/1982 | Knust et al. ................... | 424/1 |
| 4,524,059 A | | 6/1985 | Elmaleh et al. | |
| 4,764,358 A | | 8/1988 | Knapp, Jr. et al. | |

OTHER PUBLICATIONS

Degrado et al, Non–beta. –oxidizable omega. –[18F]fluoro long chain fatty Acid analogs show cytochrome P–450 mediated defluorination: implications for the design of PET tracers of myocardial fatty Acid utilization. Abs and ctation, 1992.*

Stone, CK et al; Effect of Hyperemia and Lactate Loading upon Myocardial Extraction of the Fatty Acid Analog F–18 Flouro–Thia; SCISEARCH AN 94:696070, Circulation, (10/94) vol. 90, No. 4, pT. 2 PP. 77 See abs. Oct. 1994.*

Degrado et al, Myocardial uptake of the fatty acid analog 14–flourine–18–fluoro–6–thia–heptadecanoic acid in comparison to beta–oxidation rates by tritiated palmitate, 1998.*

Stone C.K. et al. Effect of Hyperemia and Lactate Loading Upon Myocardial Extraction of the Fatty Acid Analog 18F–Fluoro–Thia–Heptadxecanoic Acid. Circulation. Nov. 14–17, 1994, vol. 90, No. 4, Part 2; pp. 77, see abstract and attached database SDCISEARCH AN 94:696070 Citation.

Scientific Papers, Proceedings of the 44$^{th}$ Annual Meeting, The Journal of Nuclear Medicine, pp. 124–125, Wednesday, Jun 4, 1997.

Journal of Labelled Compounds and Radiopharmaceuicals, vol. XXIX, No. 9, Synthesis of 14(R,S)–[$^{18}$F] Fluoro–6–Thia–Heptadecamoic Acid (FTHA); Timothy R.. DeGrado Institut für Chemie 1, Forschungszentrum Jülich, FRG, pp. 989–995.

8–[$^{18}$F]Fluorooctanoic Acid and its β–Substituted Derivatives as Potential Agents for Cerbral Fatty Acid Studies: Synthesis and Biodistribution, Fumi Nagatsugi, Shigeki Sasaki and Minoru Maeda, Facility of Pharmaeutical Sciences, Xyushu University, Naidashi 3–1–1, Higashi–ku Fukuoka 812, Japan, pp. 809–817.

14(R,S)–[$^{18}$F]Fluoro–6–Thia–Heptadecanoic Acid (FHTA): Evaluation in Mouse of a New Probe of Myocardial Utilization of Long Chain Fatty Acids, Timothy R. DeGrado, Heinz H. Coenen, and Gerhard Stocklin, Institut fur Chemie 1, Forschungszentrum Julich, Germany, pp. 1888–1896, The Journal of Nuclear Medicine, vol. 32, No. 10, Oct. 1991.

Free Fatty Acid Uptake in the Myocardium and Skeletal Muscle Using Fluorine–18–Fluoro–6–Thia–Heptadecanoic Acid, Maija T. Maki, Merja Haaparanta, Pirjo Nuutila, Vesa Oikonen, Matti Luotolahti, Olli Eskola and Juhani M. Knuuti, Departments of Nuclear Medicine, Medicine and Clinical Physiology, and Radiochemistry Laboratory, University of Turku, Turku, and Turku PET Centre, Turku, Finland, pp. 1320–1327, The Journal of Nuclear Medicine, vol. 39, No. 8, Aug. 1998.

Kinetics of 14(R, S)–Fluorine–18–Fluoro–6–Thia–Heptadecanoic Acid in Normal Human Hearts at Rest, During Exercise and After Dipyridamole Injection, Andreas Ebert, Hans Herzog, Gerhard L. Stocklin, Michael M. Henrich, Timothy R. DeGrado, Heniz H. Coenen and Ludwig E. Feinendegen, Institute fur Medizin und Nuklearchemie, Forschungszentrum Julich, and Nuklennedizinische Klinik der Heinrich–Heine–Universital Dusseldorf, Julich, Germany, pp. 51–56, The Journal of Nuclear Medicine, vol. 35, No. 1, Jan. 1994.

Myocardial Uptake of the Fatty Acid Analog 14–Fluorine–18–Fluoro–6–Thia–Heptadecanoic Acid in Comparison to Beta–Oxidation Rates by Tritiated Palmitate, Charles k. Stone, Robert A. Pooley, Timothy R. DeGrado, Britta Renstrom, Robert J. Nickles, Stephen H. Nellis, A. James Liedtke and James E. Holden; Departments of Medicine (Cardiology), Radiology (Nuclear Medicine) and Medical Physics, University of Wisconsin–Madison, Madison, Wisconsin; and Department of Radiology, Duke University, Durham, North Carolina; The Journal of Nuclear Medicine, vol. 39, No. 10, Oct. 1998.

(List continued on next page.)

Primary Examiner—Deborah D. Carr
(74) Attorney, Agent, or Firm—Nixon & Vanderhye P.C.

(57) ABSTRACT

Sulfur heteroatom substitution at the C4 position of $^{18}$F-labeled fatty acids yields a tracer that is retained in proportion to the beta-oxidation rates in mammalian tissue, particularly hypoxic myocardium. Most preferably, the invention is embodied in an [$^{18}$F]fluoro-4-thia-fatty acid having a chain length of between 8 to 20 carbon atoms. The $^{18}$F-labeled 4-thia fatty acids of this invention find particular utility the radiolabelling of tissue sites (e.g., myocardium) for purposes of positron emission tomography.

13 Claims, No Drawings

OTHER PUBLICATIONS

Comparison of Fatty Acid Tracers FTHA and BMIPP During Myocardial Ischemia and Hypoxia, Britta Renstrom, Stephen Rommelfanger, Charles K. Stone, Timothy R. DeGrado, Khristen J. Carlson, Emanual Scarbrough, Robert J. Nickles, A. James Liedtke and James E. Holden; Department of Medicine (Cardiology), Radiology and Medical Physics, University of Wisconsin–Madison, Madison, Wisconsin, and Department of Radiology, Duke University Medical Center, Durham, North Carolina, pp. 1684–1689, The Journal of Nuclear Medicine, vol. 39, No. 10, Oct. 1998.

Database HCAPLUS on STN, Accession No. 1992:403405, DeGrado et al, Non–beta.–oxidizable .omega—[18F]fluoro long chain fatty acid analogs show cytochrome P–450–mediated defluorination: implications for the design of PET tracers of myocardial fatty acid utilisation. Nucl. Med. Biol. 1992, 19(3), 389–97.

Circulation, vol. 90, No. 4, Part 2, Oct. 1994, Abstracts From the 67th Scientific Session, Dallas Convention Center, Dallas, Texas, Nov. 14–17, 1994, 73–3173(SP) ISSN 0009–7322.

Database HCAPLUS on STN, Accession No. 1998–695285, Stone, 'Myocardial uptake of the fatty acid analog 14–fluorine–18–fluoro–6–thia–heptadecanoic acid in comparison to beta–oxidation rates by tritiated palmitate'. J, Nucl. Med. (1998), 39(10), 1690–1696.

* cited by examiner

F18-LABELED THIA FATTY ACIDS AND METHODS OF MAKING AND USING THE SAME

CROSS-REFERENCE TO RELATED APPLICATION

This application is based on, and claims domestic priority benefits under 35 USC §119(e) from, U.S. Provisional Patent Application Ser. No. 60/129,913 filed on Apr. 19, 1999, the entire content of which is expressly incorporated hereinto by reference.

FIELD OF THE INVENTION

The present invention relates to $^{18}$F-labeled thia fatty acids, and to methods of making and using the same, in particular, to methods of using such fatty acids as a tracer compound in positron emission tomography (PET).

BACKGROUND OF THE INVENTION

A radioiodinated 4-thia fatty acid analog has been previously reported (Gildehaus et al, J Nucl Med 38:124P, 1997, abstract). $^{18}$F-labeled fatty acids are known generally from U.S. Pat. No. 4,323,547 (incorporated hereinto by reference) as useful in PET studies of myocardial metabolism. More recently, $^{18}$F-labeled 6-thia fatty acid (14F6THA) has been synthesized and evaluated (DeGrado, J Lab Compd Radiopharm 24:989–995,1991; DeGrado et al, J Nucl Med 32:1888–1896, 1991, each incorporated hereinto fully by reference). Although 14F6THA tracks beta-oxidation of palmitate in a number of conditions, it was found to be insensitive to inhibition of beta-oxidation in myocardium in conditions of hypoxia with normal blood flow. Retention of tracer in hypoxic myocardium likely reflects retention of metabolic intermediates that precede beta-oxidation (long chain acyl-CoA, acyl-carnitine, and/or esterified lipids).

SUMMARY OF THE INVENTION

The present invention is based on the discovery that sulfur heteroatom substitution at the C4 position, instead of the C6 position, of $^{18}$F-labeled fatty acids yields a tracer that is retained in proportion to the beta-oxidation rates in normoxic and hypoxic mammalian tissue, particularly normoxic and hypoxic myocardium. Most preferably, the invention is embodied in an [$^{18}$F]fluoro-4-thia-fatty acid having a chain length of between 8 to 20 carbon atoms, and may be saturated or at least partially unsaturated (i.e., contain one or more double bonds).

The $^{18}$F-labeled 4-thia fatty acids of this invention find particular utility in the noninvasive assessment of regional beta-oxidation rates using PET techniques which may allow early detection of abnormalities in the myocardium that might presage irreversible tissue injury.

Although not wishing to be bound to any particular theory, it is surmised that the 4-thia intermediates that precede beta-oxidation are poorly retained in the myocardium, possibly due to facile hydrolysis of the CoA and/or carnitine esters.

The [$^{18}$F]fluoro-4-thia-fatty acids according to this invention are most conveniently synthesized by subjecting a hydrolyzable ester precursor of a 4-thia-fatty acid having a readily substitutable group at the terminal carbon or an odd-numbered carbon from the terminal carbon to $^{18}$F substitution conditions. Thereafter, the $^{18}$F-substituted hydrolyzable ester precursor of the 4-thia fatty acid may be subjected to hydrolysis conditions to form the corresponding [$^{18}$F]fluoro-4-thia-fatty acid. Most preferably, the readily substitutable group is selected from bromo, iodo, tosylate, benzenesulfonylate and the like, while the group that makes the precursor readily hydrolyzable may be benzyl, methyl and the like. By way of example, methyl 16-bromo-4-thia-hexadecanoate is a synthetic precursor of 16-[$^{18}$F]fluoro-4-thia-hexadecanoic acid. Bromo and iodo esters are preferable since their respective acids are easily separated from the radioactive product fatty acid.

The precursor is synthesized by conventional organic synthesis techniques. For example, methyl 16-bromo-4-thia-hexadecanoate is synthesized by reaction of methyl 3-mercaptopropionate with 1,12-dibromododecane in acetonitrile in the presence of potassium carbonate. The product ester is separated from reactants and other reaction products by silica gel liquid chromatography (hexane/ether 3:1, $R_f$=0.6). Labeling at the ω-3 position requires two additional synthetic steps preceding the condensation reaction with methyl 3-mercaptopropionate, namely oxidation of ω-bromo-(1)alcohol to the (ω-bromo(1)aldehyde in dichloromethane using pyridinium chlorochromate followed by reaction of the aldehyde with propyl magnesium chloride in ether. The resultant (ω-3)-alcohol is then condensed with methyl 3-mercaptopropionate to yield the hydroxyester. The hydroxyester is converted to the corresponding tosyloxyester by reaction with Ts-Cl in pyridine. Finally, the tosyloxyester is converted to the bromide, for example, by reaction with LiBr in acetone. Liquid chromatography is used at each step to isolate the products. $^{18}$F labeling may then conventionally be carried out as described in the literature cited above.

A further understanding of this invention will be obtained from the following non-limiting Examples.

EXAMPLES

In the Examples which follow, four $^{18}$F-labeled thia fatty acids were synthesized and evaluated: (1) 10-[$^{18}$F]Fluoro-4-thia-decanoic acid (10F4TDA), (2) 16-[$^{18}$F]Fluoro-4-thia-hexadecanoic acid (16F4THA, FTP), (3) 13(R,S)-[$^{18}$F]Fluoro-4-thia-hexadecanoic acid (13F4THA), and for comparative purposes (4) 17-[$^{18}$F]Fluoro-6-thia-heptadecanoic acid (17F6THA).

Chemicals were of analytical grade. Dry acetonitrile was obtained commercially (Pierce, Rockford, Ill.). $^{1}$H-NMR spectra were recorded with a Varian Unity 500 MHz spectrometer using CDCl$_3$ as solvent (Me$_4$Si, 0.00 ppm). $R_f$ values refer to thin layer chromatography (TLC) performed on silica gel with the solvent system noted. Routine column chromatography was performed under normal pressure with silica gel (100–200 mesh) and the solvent system noted.

(1) Synthesis of Methyl 16-iodo-4-thia-hexadecanoate 1,12-diiodododecane (2.66 g, 6.3 mmol) was dissolved in 20 mL acetonitrile. Methyl 3-mercaptopropionate (0.76 g, 6.3 mmol) and K$_2$CO$_3$ (1.1 g, 8 mmol) were added and the mixture was allowed to react at room temperature for 20 h. The mixture was acidified with ice-diluted HCl and the solution was extracted twice with ether (20 mL). The combined ether fractions were washed successively with dilute NaHCO$_3$, water and brine, dried (MgSO$_4$) and evaporated under reduced pressure. The product 1 (0.84 g, 32% yield) was isolated by column chromatography (hexane/ethyl acetate 9:1) and recrystallized in MeOH. TLC (hexane/ethyl acetate 9:1) $R_f$=0.4. Melting point=33° C. $^{1}$H-NMR δ1.4 (m, 20H, CH$_2$), 2.52 (t, 2H, C(2)H$_2$), 2.61 (t, 2H, C(5)H$_2$), 2,79 (t, 2H, C(3)H$_2$), 3.20 (t, 2H, C(16)H$_2$), 3.71 (s, 3H, —COO—CH$_3$).

(2) Synthesis of 16-Fluoro-4-thia-hexadecanoic acid

Fluorination of 1 (0.2 g, 0.5 mmol) was performed by addition of tetrabutylammonium fluoride (TBAF) (4 mmol as 1M THF solution). The mixture was allowed to react at room temperature for 20 h. The resulting fluoro-ester was hydrolyzed by addition of 1 ml 1 N KOH and 1 ml ethanol for 2 h at room temperature. The product 2 (0.05 g, 34% yield) was isolated by column chromatography (hexane/ether/acetic acid 3:1:0.1) and recrystallized in hexane, TLC (hexane/ether/acetic acid 3:1:0.1) $R_f$=0.25. Melting point= 59° C., $^1$H-NMR δ1.4 (m, 20H, $CH_2$), 2.55 (t, 2H, C(2)$H_2$), 2.65 (t, 2H, C(5)$H_2$), 2.80 (t, 2H, C(3)$H_2$), 4.44 (dt, 2H, C(16)$H_2 J_{HH}$=6.2 Hz).

(3) Synthesis of Methyl 17-tosyloxv-6-thia-heptadecanoate

To a solution of 11-bromo-1-undecanol (10 g, 40 mmol) in DMSO (80 mL) was added thiourea (3.64 g, 48 mmol), and the mixture was allowed to react at room temperature for 21 hr. The mixture was extracted twice with hexane (20 mL) to remove the unreacted bromo alcohol. To the DMSO fraction was added 2N KOH (50 mL) and the mixture was heated at 80° C. for 5 min, releasing the thiol 11-mercapto-undecanol. The mixture was acidified (HCl) and extracted twice with ether (40 ml). The combined ether phases were washed successively with water and brine, dried over $MgSO_4$, and evaporated under reduced pressure. The resulting thiol (≅7.2 g) was caused to react with methyl 5-bromo-pentanoate (7 g, 37 mmol) according to the procedure for compound 1. Crystallization of the product in hexane yielded 5.5 g (18 mmol 48% yield from the thiol) of methyl 17-hydroxy-6-thia-heptadecanoate. TLC (hexane/ether 1:1) showed a single product at $R_f$=0.3. Without further characterization, the hydroxy-ester (4 g, 12 mmol) was caused to react with Ts-Cl (2.7 g, 12 mmol) and pyridine (14 mmol) in $CHCl_2$(40 mL) at 5° C. for 4 hr. The mixture was acidified with ice-diluted HCl, and the organic layer separated, dried ($MgSo_4$) and evaporated under reduced pressure. The product 3 (2.4 g, 34% yield) was isolated by column chromatography (hexane/ethyl acetate 7:3) and recrystallized in hexane. TLC (hexane/ethyl acetate 7:3) $R_f$=0.6. Melting point=54° C. $^1$H-NMR δ1.3 (m, 22H, $CH_2$), 2.38 (t. 2H, C(2)$H_2$), 2.5 (m, 7H, C(5)$H_2$, C(7)$H_2$, (tosyl) $CH_3$), 3.7 (s, 3H, —COO—$CH_3$), 4.0 (t, 2H, C(17)$H_2$), 7.6 (m, 4H, aryl).

(4) Synthesis of 17-Fluoro-6-thia-heptadecanoic acid Compound 3 (1 g, 1.8 mmol) was caused to react with TBAF (2–5 mmol) according to the procedure for compound 2. The resultant fluoroester was hydrolyzed in KOH/ethanol as previously described, and crystallized twice in ethanol/water to yield 0.4 g (70% yield) product 4. Melting point=54° C. $^1$H-NMR δ1.3 (m, 22H, $CH_2$), 2.38 (t, 2H, C(2)$H_2$), 2.5 (m, 4H, C(5)$H_2$, C(7)$H_2$), 4.44 (dt, 2H, C(17)$H_2$, $J_{HF}$=47.3, $J_{HH}$=6.2 Hz).

(5) Synthesis of Methyl 10-bromo-4-thia-decanoate 1,6-dibromo-hexane (1.6 g. 13 mmol) and methyl 3-mercapto-propionate (13 mmol) were caused to react according to the procedure for compound 1. The product 5 (1.3 g, 35% yield) was isolated as an oil by column chromatography (hexane/ether 1:1). TL (hexanelether 1:1) $R_f$=0.6. $^1$H-NMR δ1.4 (m, 12H, $CH_2$), 2.52 (t, 2H, C(2)$H_2$), 2.61 (t, 2H, C(5)$H_2$), 2.8 (t, 2H, C(3)$H_2$), 3.40 (t, 2H, C(10)$H_2$), 3.7 (s, 3H, COO—$CH_3$).

(6) Synthesis of 10-Fluoro-4-thia-decanoic acid

Compound 5 (0.5 g, 1,8 mmol) was caused to react with TBAF (3 mmol) according to the procedure for compound 2. The resultant fluoroester was hydrolyzed in KOH/ethanol as previously described, and isolated as an oil by HPLC (Table 1) to yield 0.14 g (37% yield) product 6. $^1$H-NMR δ1.3 (m, 8H, $CH_2$), 2.55 (t, 2H, C(2)$H_2$), 2,65 (t,2H, C(5)$H_2$), 2.80 (t, 2H, C(3)$H_2$), 4.44 (dt, 2H, C(16)$H_2 J_{HF}$=47.5 Hz, $J_{HH}$=6.2 Hz).

(7) Methyl 13(R,S)-hydroxy-4-thia-hexadecanoate

To a solution of 12-bromo-3-dodecanol (8.78 g, 33.1 mmol) in acetonitrile (80 mL) was added methyl 3-mercaptopropionate (3–98 g. 33.1 mmol) and $K_2CO_3$ (5,5 g, 40 mmol). The mixture was allowed to react at room temperature for 20 hr. The mixture was acidified with ice-diluted HCl and the solution was extracted twice with ether (40 mL). The combined ether fractions were washed successively with dilute $NaHCO_3$, water and brine, dried ($MgSO_4$) and evaporated under reduced pressure. The product 7 (4.4 g, 44% yield) was isolated by column chromatography (hexane/ether 1:1) and recrystallized in hexane. TLC (hexane/ether 1:1) $R_f$=0.4. Melting point=38.8° C. $^1$H-NMR δ0.93 (t, 3H, C(16)$H_2$), 1.4 (m, 18H, $CH_2$), 2.52 (t, 2H, C(2)$H_2$), 2.61(t, 2H, C(5) $H_2$), 2.79 (t, 2H, C(3)$H_2$), 3.60 (m, 1H, C(13)H), 3.70 (s, 3H,—COO—$CH_3$).

(8) Methyl 12(R,S)-benzenesulfonyloxy-4-thia-hexadecanoate

Compound 7 (0.83 g, 2.7 mmol) was caused to react with benzenesulfonylchloride (0.45 ml, 3.5 mmol) and pyridine (3.5 mmol) in $CHCl_2$ (20 mL) at 5° C. for 20 hr. The mixture was ice-diluted HCl, and the organic layer separated, dried ($MgSO_4$ and evaporated under reduced pressure. The product 8 (1.0 g. 83% yield) was isolated as an oil by column chromatography (hexane/ether 1:1). TLC (hexane/ether 1:1) $R_f$=0.5. $^1$H-NMR δ0.82 (t, 3H, C(16)$H_2$), 1.4 (m, 18H, $CH_2$), 2.52 (t, 2H, C(2)$H_2$), 2.62 (t, 2H, C(5)$H_2$), 2.78 (t, 2H, C(3)$H_2$ 3.70 (s, 3H, —COO—$CH_3$), 4.60 (m, 1H, C(13)H), 7.7 (m, 5H, aryl).

(9) 13(R,S)-Fluoro-4-thia-hexadecanoic acid

Compound 11 (0.5 g, 1.1 mmol) was caused to react with TBAF (2.5 mmol) according to the procedure for compound 2. The resultant fluoro-ester was hydrolyzed in KOH/ethanol as previously described, and crystallized twice in hexane to yield product 12 (0.12 g, 44% yield). TLC (hexane/ether/AcOH 1:2:0.03) $R_f$=0.6 Melting point=61° C. $^1$H-NMR δ0.94 (t, 3H, C(16)$H_2$), 1.4 (m, 18H, $CH_2$), 2.52 (t, 2H, C(2)$H_2$), 2.62 (t, 2H, C(5)$H_2$), 2.78 (t, 2H, C(3)$H_2$),4.47 (double septuplet, 1H, C(13)H, $J_{HF}$=49.3 Hz $J_{HH}$=3.8 Hz).

$^{18}$F-labeling procedure

The precursors for 16F4THA, 13F4THA, 10F4THA, and 17F6THA were compounds 1, 8, 5, and 3, respectively. To a 2 ml glass vial was added Kryptofix 2.2.2 (10 mg), acetonitrile (0.5 ml) and 20 μl of a 9% $K_2CO_3$ solution in water. [$^{18}$F]Fluoride, produced via proton bombardment of $H_2^{18}$O (>95 atom %), was then added, the vessel placed in an aluminum heating block at 90° C., and the solvent evaporated under a stream of helium or nitrogen. The residue was further dried by azeotropic distillation with acetonitrile (2×0.3 ml). A solution of the precursor (~2 mg) in acetonitrile (0.5 ml) was added, the vial was sealed and returned to the heating block. Reaction time was 15 min. The vial was briefly cooled by placing in ice-water. The incorporation of [$^{18}$F]fluoride was monitored by radio-TLC (hexane/ethyl acetate 3:1). $R_f$ values were 0.0 and >0.4 for [$^{18}$F]fluoride and [$^{18}$F]fluoro-ester, respectively, Subsequent hydrolysis of the resulting [$^{18}$F]fluoro-ester was performed in the same vessel by the addition of 0.2 ml 0.2N KOH and continued heating at 90° C. for 4 min. The mixture was cooled, acidified with concentrated acetic acid (25 μl), filtered, and applied to the preparative HPLC column (Table 1). The [$^{18}$F]fluoro-fatty acid fraction was collected, evaporated to dryness, formulated In isotonic NaCl solution (for long-chain fatty acid analogs, 1–2% albumin was present), and filtered through a 0.22 μm filter (Millex-GS).

TABLE 1

Semi-preparative reverse phase HPLC capacity factors (k') of fatty acid analogs (Nucleosil, C-18 (10μ), 250 × 10 mm, flow = 4.3 ml/min, mobile phase is MeOH/H$_2$O/AcOH X:Y:0.5, X + Y = 99.5)

| Compound | Mobile Phase (% MeOH) | k' |
|---|---|---|
| 16-Iodo-4-thia-hexadecanoic acid | 90 | 5.1 |
| 16-Fluoro-4-thia-hexadecanoic acid (2,16F4THA, FTP) | 90 | 3.2 |
| 13-Benzenesulfonyloxy-4-thia-hexadecanoic acid | 90 | 2.7 |
| 13-Fluoro-4-thia-hexadecanoic acid (9,13F4THA) | 90 | 3.5 |
| 17-Tosyloxy-6-thia-heptadecanoic acid | 90 | 3.0 |
| 17-Fluoro-4-thia heptadecanoic acid (4,17F6THA | 90 | 3.5 |
| 10-Bromo-4-thia-decanoic acid | 70 | 4.3 |
| 10-Fluoro-4-thia-decanoic acid (6,10F4TDA) | 70 | 2.7 |

Biological Studies

Model 4-thia analogs (16-[$^{18}$F]fluoro-4-thia-hexadecanoic acid and 12-[$^{18}$F]fluoro-4-thia-dodecanoic acid) were examined as tracers in isolated rat hearts. The perfusate was Krebs-Hensleit buffer with 1% albumin, 0.15 mM palmitate, and 5 mM glucose. Sprague Dawley rats (200–225 g) were fed ad libetum. The hearts were excised from pentobarbital-anesthetized animals and perused at 7 ml/min in Langendorff retrograde fashion. The perfusate was gassed with either 95% oxygen (normoxic) or 35% oxygen (hypoxic) gas mixture. The gases comprising the remaining fraction were nitrogen and carbon dioxide (5% for both). The tracer was administered as a bolus or as a pulse infusion into the isolated rat hearts. Pulse infusion allowed absolute quantification of $^{18}$F accumulation rates that reflect the metabolic rate of the tracer in the heart. Clearance rates are measured during the washout phase of these experiments. Beta-oxidation rates of 9,10[$^3$H] palmitate were measured by collection of venous effluent samples and separation of titrated water. Results showed good correlation of beta-oxidation rates with uptake rates of the model 4-thia analogs (r>0.86) for both normoxic and hypoxic conditions. In contrast, the 6-thia analog (17F6THA) showed poor correlation with beta-oxidation rates in the same conditions.

PET imaging studies were performed with 16F4THA in patients with ischemic cardiomyopathy. Conventional nuclear medicine perfusion scans were obtained in the same subjects. The PET scans were of superior quality to the conventional nuclear scans and showed different information form the perfusion images, possibly reflecting greater sensitivity to ischemia.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An $^{18}$F-labeled thia fatty acid tracer which is the compound [$^{18}$F]fluoro-4-thia-fatty acid that exhibits a retention rate that is in substantial proportion to the beta-oxidation rate in normoxic and hypoxic myocardium.

2. The $^{18}$F-labeled thia fatty acid tracer of claim 1, having an saturated or at least partially unsaturated chain length between 8 to 20 carbon atoms.

3. The $^{18}$F-labeled thia fatty acid tracer of claim 1, wherein the [$^{18}$F]fluoro atom is substituted at the terminal carbon or at an odd-numbered carbon from the terminal carbon.

4. The $^{18}$F-labeled thia fatty acid tracer of claim 3, which is one selected from the group consisting of 13-[$^{18}$F]fluoro-4-thia-hexadecanoic acid, 16-[$^{18}$F]fluoro-4-thia-hexadecanoic acid and 10-[$^{18}$F]fluoro-4-thia-decanoic acid.

5. An $^{18}$F-labeled thia fatty acid tracer for mammalian tissue which comprises the compound [$^{18}$F]fluoro-4-thia-fatty acid.

6. The tracer of claim 4, wherein the compound has a chain length between 8 to 20 carbon atoms.

7. The tracer of claim 4, wherein the [$^{18}$F]fluoro atom is substituted at the terminal carbon or at an odd-numbered carbon from the terminal carbon.

8. The tracer of claim 7, wherein the compound is one selected from the group consisting of 13-[$^{18}$F]fluoro-4-thia-hexadecanoic acid, 16-[$^{18}$F]fluoro-4-thia-hexadecanoic acid and 10-[$^{18}$F]fluoro-4-thia-decanoic acid.

9. The compound [$^{18}$F]fluoro-4-thia-fatty acid having a chain length between 8 to 20 carbon atoms which is at least partially unsaturated.

10. A method of radiolabeling mammalian tissue which comprises administering to a mammal having a tissue site in need of radiolabeling a radiolabeling effective amount of the $^{18}$F-labeled thia fatty acid tracer according to any one of claims 1–8.

11. The method of claim 10, wherein the mammalian tissue is myocardium.

12. A positron emission tomography method which comprises radiolabeling a mammalian tissue site by administering to the site a radiolabeling effective amount of the $^{18}$F-labeled thia fatty acid tracer according to any one of claims 1–8, and thereafter subjecting the radiolabeled mammalian tissue site to positron emission tomography, and generating an image therefrom.

13. The method of claim 12, wherein the mammalian tissue is myocardium.

* * * * *

UNITED STATES PATENT AND TRADEMARK OFFICE
CERTIFICATE OF CORRECTION

PATENT NO.     : 6,362,352 B1
DATED          : March 26, 2002
INVENTOR(S)    : Timothy R. DeGrado et al.

It is certified that error appears in the above-identified patent and that said Letters Patent is hereby corrected as shown below:

<u>Column 5,</u>
Line 49, change "form" to -- from --

Signed and Sealed this

Twenty-eighth Day of May, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,362,352 B1
DATED : March 26, 2002
INVENTOR(S) : Timothy R. DeGrado et al.

It is certified that error appears in the above-identified patent and that said Letters Patent is hereby corrected as shown below:

Column 1,
Line 4, add the following prior to the title "CROSS-REFERENCE TO RELATED APPLICATION":
-- This invention was made with Government support under Grant No. R29-HL54882 awarded by the National Instituted of Health. The Government has certain rights in the invention. --

Signed and Sealed this

Fourth Day of January, 2005

JON W. DUDAS
*Director of the United States Patent and Trademark Office*

UNITED STATES PATENT AND TRADEMARK OFFICE
CERTIFICATE OF CORRECTION

PATENT NO.   : 6,362,352 B1
DATED        : March 26, 2002
INVENTOR(S)  : Timothy R. DeGrado et al.

It is certified that error appears in the above-identified patent and that said Letters Patent is hereby corrected as shown below:

Column 1,
Line 4, prior to the title "CROSS-REFERENCE TO RELATED APPLICATION":
"This invention was made with Government support under Grant No. R29-HL54882 awarded by the National Instituted of Health. The Government has certain rights in the invention." (as added by Certificate of Correction issued January 4, 2005.)

This certificate supersedes Certificate of Correction issued January 4, 2005.

Signed and Sealed this

Twenty-ninth Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,362,352 B1
DATED : March 26, 2002
INVENTOR(S) : Timothy R. DeGrado et al.

It is certified that error appears in the above-identified patent and that said Letters Patent is hereby corrected as shown below:

Column 1,
Line 4, prior to the title "CROSS-REFERENCE TO RELATED APPLICATION":
"This invention was made with Government support under Grant No. R29-HL54882 awarded by the National Instituted of Health. The Government has certain rights in the invention." (as added by Certificate of Correction issued January 4, 2005 and March 29, 2005.) delete the statement in it's entirety.

Signed and Sealed this

Twelfth Day of July, 2005

JON W. DUDAS
*Director of the United States Patent and Trademark Office*